United States Patent
Xie et al.

(10) Patent No.: US 10,538,711 B2
(45) Date of Patent: Jan. 21, 2020

(54) PROCESS FOR CONVERTING NAPHTHA

(71) Applicants: SABIC GLOBAL TECHNOLOGIES B.V., Bergen Op Zoom (NL); DALIAN INSTITUTE OF CHEMICAL PHYSICS, CHINESE ACADEMY OF SCIENCES, Dalian (CN)

(72) Inventors: Peng Xie, Dalian (CN); Mingzhi Li, Dalian (CN); Yunpeng Xu, Dalian (CN); Guangye Liu, Dalian (CN); Zhongmin Liu, Dalian (CN); Haitao Liu, Shanghai (CN)

(73) Assignees: SABIC GLOBAL TECHNOLOGIES B.V., Bergen Op Zoom (NL); DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 15/578,831

(22) PCT Filed: Jun. 2, 2015

(86) PCT No.: PCT/CN2015/080591
§ 371 (c)(1),
(2) Date: Dec. 1, 2017

(87) PCT Pub. No.: WO2016/192041
PCT Pub. Date: Dec. 8, 2016

(65) Prior Publication Data
US 2018/0163147 A1    Jun. 14, 2018

(51) Int. Cl.
*C10G 63/04* (2006.01)
*C10G 69/04* (2006.01)

(52) U.S. Cl.
CPC .......... *C10G 69/04* (2013.01); *C10G 2400/20* (2013.01); *C10G 2400/22* (2013.01); *C10G 2400/30* (2013.01)

(58) Field of Classification Search
CPC .............. C10G 69/04; C07C 4/04; C07C 4/06
(Continued)

(56) References Cited

U.S. PATENT DOCUMENTS 3,706,654 A * 12/1972 Bryson .................. C10G 11/18
208/113
4,137,151 A *  1/1979 Csicsery ................ B01J 29/072
208/120.01
(Continued)

FOREIGN PATENT DOCUMENTS

CN          1395609          2/2003
CN          1651363          8/2005
(Continued)

OTHER PUBLICATIONS

International Search Report and Written Opinion issued in International Application No. PCT/CN2015/080591, dated Mar. 8, 2016.
(Continued)

*Primary Examiner* — Philip Y Louie
(74) *Attorney, Agent, or Firm* — Norton Rose Fulbright US LLP (57) ABSTRACT

A process for converting naphtha, lower olefin, light aromatic hydrocarbon, and gasoline with a high octane number by combining catalytic cracking of naphtha with steam cracking of lower alkane and catalytic cracking of higher alkanes and higher olefins. The process increases the yield of product with high value and significantly decreases the yield of low value product. At the same time, the power consumption is decreased as a whole since most reactants are converted in catalytic cracking at a lower temperature.

15 Claims, 3 Drawing Sheets

(58) Field of Classification Search
USPC .... 585/476, 648, 650, 653; 208/67, 72, 113, 208/114, 120.01
See application file for complete search history.

(56) References Cited

U.S. PATENT DOCUMENTS

| | | | | |
|---|---|---|---|---|
| 5,523,502 | A * | 6/1996 | Rubin | C07C 11/04 568/697 |
| 5,856,607 | A * | 1/1999 | Kim | C07C 15/073 585/314 |
| 6,835,863 | B2 * | 12/2004 | Chester | C10G 35/095 208/120.01 |
| 10,160,922 | B2 * | 12/2018 | Funk | C10G 63/04 |
| 2002/0003103 | A1 * | 1/2002 | Henry | C10G 11/18 208/106 |
| 2007/0209969 | A1 * | 9/2007 | Shen | B01J 29/005 208/133 |
| 2010/0010279 | A1 * | 1/2010 | Kumar | B01J 27/18 585/653 |
| 2015/0174559 | A1 * | 6/2015 | Smith | B01J 29/088 208/114 |

FOREIGN PATENT DOCUMENTS

| | | |
|---|---|---|
| CN | 1665911 | 9/2005 |
| CN | 101362669 | 2/2009 |
| CN | 102795958 | 11/2012 |
| EP | 1734098 | 12/2006 |
| EP | 2660228 | 11/2013 |
| WO | WO 1999/041331 | 8/1999 |

OTHER PUBLICATIONS

European Search Report issued in European Patent Application No. 15893697 dated Jan. 4, 2019.

* cited by examiner

PROCESS FOR CONVERTING NAPHTHA

This application is a national phase under 35 U.S.C. § 371 of International Application No. PCT/CN2015/080591, filed Jun. 2, 2015, and Chinese Patent Application No. 201510296090.8 ("Transformation method for naphtha") filed on Jun. 2, 2015. The entire contents of each of the above-referenced applications are incorporated into the present application by reference.

FIELD OF THE INVENTION

The present application relates to a process for converting naphtha and belongs to the petrochemical field.

DESCRIPTION OF THE RELATED ART

The production of chemical products, such as ethylene and propylene, from high-temperature steam cracking of naphtha is an enormous petrochemical industry. Every year, hundreds of millions of tons of naphtha are used in this process. After many years of development, steam cracking technologies have reached a very high level and a high rate of conversion can be achieved. The product yield can be high after only one reaction. The drawbacks thereof include poor selectivity, production of a large quantity of methane in the products, high reaction temperature, and high energy consumption. In light of this, people have been developing catalytic cracking technologies to produce alkenes in past decades, which are used to crack naphtha and other proper raw materials to produce lower alkenes.

Catalytic cracking is characterized by relatively low reaction temperature and high selectivity. However, its rate of conversion with regard to lower hydrocarbons is low. When using cycloalkyl and intermediate base naphtha as the raw material, the product yield of single pass conversion by currently reported technologies is not high enough to compete against hydrothermal cracking. This is the main reason why, after many years of development of catalytic cracking technologies, industrial applications of the technologies have not been achieved to produce alkenes through catalytic cracking of naphtha. In addition, the catalysts use molecular sieves as the active ingredient. Under reaction conditions, aluminum, as the molecular sieve skeleton, gradually escapes due to the high-temperature steam, and the activity of the catalysts is gradually weakened, thereby leading to lowered conversion rate of reactants. Such a technical difficulty has not been solved either.

SUMMARY OF THE INVENTION

According to one aspect of the present application, a process for converting naphtha is provided, which combines catalytic cracking and high-temperature steam cracking of naphtha to produce lower alkenes, aromatic hydrocarbons, and gasoline with high octane numbers. This process significantly increases the yield of high-value products and lowers the yield of low-value products; at the same time, since most of the reactants are converted in catalytic cracking at a relatively low temperature, the overall energy consumption can be lowered.

The process for converting naphtha is characterized in that it at least comprises the following steps:

a) sending a feed that contains naphtha into a first reaction zone to contact and react with a catalyst that contains a molecular sieve at a reaction temperature of 580° C. to 700° C., and separating the reaction products to obtain a material flow I and a product I;

b) sending a steam and the material flow I obtained in the step a) into a second reaction zone to undergo a steam cracking reaction at a reaction temperature of 780° C. to 870° C., and obtaining a product III after the reaction;

the material flow I comprises alkanes with a carbon atom number of 2 to 5;

the product I comprises alkenes with a carbon atom number of 2 to 12, aromatic hydrocarbons with a carbon atom number of 6 to 12, and alkanes with a carbon atom number of 6 to 12;

the product III comprises lower alkenes with a carbon atom number of 2 to 4 and aromatic hydrocarbons with a carbon atom number of 6 to 8.

The reaction products in the first reaction zone are separated to obtain the material flow I and the product I, and the remainder is a byproduct I. The byproduct I mainly comprises hydrogen gas and methane.

The reaction products in the second reaction zone are separated to obtain the product III, and the remainder is a byproduct III. The byproduct III mainly comprises hydrogen gas and methane.

In the alkenes with a carbon atom number of 2 to 12 in the product I, there are mainly lower alkenes with a carbon atom number of 2 to 4. In the aromatic hydrocarbons with a carbon atom number of 6 to 12 in the product I, there are mainly aromatic hydrocarbons with a carbon atom number of 6 to 8. In the alkanes with a carbon atom number of 6 to 12 in the product I, there are mainly isoalkanes and cycloalkanes that contain branched chains. All main components in the product I have high economic values. The lower alkenes with a carbon atom number of 2 to 4 and the aromatic hydrocarbons with a carbon atom number of 6 to 8 in the product I can be used as important raw materials in chemical industry; the isoalkanes, cycloalkanes that contain branched chains, and aromatic hydrocarbons with a carbon atom number of 9 to 12 in the product I can all be used to produce gasoline with high octane numbers. The process according to the present application can obtain a lot of the above products with high values from the reaction of the raw material naphtha.

The reaction features of catalytic cracking include relatively low reaction temperature and good selectivity, but it has a low rate of conversion for alkanes with a carbon atom number of 2 to 5; steam cracking is characterized by a high rate of reactant conversion, but it has relatively low selectivity, high reaction temperature and high energy consumption. The present application selectively combines these two cracking processes to make use of advantageous aspects of the two cracking processes, respectively, such that the reactants first undergo a catalytic cracking reaction at relatively low reaction temperature in the first reaction zone, most materials produce the product in a highly selective manner, and the remaining components suitable for steam cracking undergo steam cracking in the second reaction zone. The reaction products are output or stored. Here, the alkanes with a carbon atom number of 2 to 5 include ethane, propane, butane and pentane, which are difficult to effectively convert in the catalytic cracking reaction and also have very low economic values. However, they have shown advantages in conversion, in particular in the aspect of selectivity, in the steam cracking reaction. The alkanes with a carbon atom number of 2 to 5 are separated from the reaction products in the first reaction zone and undergo steam cracking, and the products thereof mainly include lower alkenes and light aromatic hydrocarbons, which have far greater economic values than the alkanes with a carbon atom number of 2 to 5 do. At the same time, as the total amount of the alkanes with a carbon atom number of 2 to 5 in the reaction products from the first reaction zone is relatively low, the energy consumption required by steam cracking in the second reaction zone is not high. In summary, the present application changes the understanding of applications of steam cracking in the prior art, and selectively performs steam cracking only on the component of alkanes with a carbon atom number of 2 to 5 with low economic values, low production and difficulty in catalytic conversion. By only slightly increasing the energy consumption, the present application converts most of the components with very low economic values to products with very high economic values. A more suitable and more efficient process is used to convert a low-value component to a high-value component, which significantly improves the economic advantages as a whole.

In the present application, "alkanes" comprise linear alkanes and cycloalkanes.

In the present application, "lower alkenes with a carbon atom number of 2 to 4" comprise ethylene, propylene, 1-butylene, 2-butylene, isobutylene, and 1,3-butadiene, which are referred to as lower alkenes in short.

In the present application, "aromatic hydrocarbons with a carbon atom number of 6 to 8", also referred to as light aromatic hydrocarbon or BTX in short, comprise benzene, toluene and xylene.

In the present application, "naphtha" comprises full range naphtha and/or naphtha having partial fractions. Typical naphtha having partial fractions includes naphtha from the initial boiling point to 150° C. (IBP—150° C. in short) and naphtha from the initial boiling point to 180° C. (IBP—180° C. in short).

According to another aspect of the present application, a process for converting naphtha is provided, which combines catalytic cracking and high-temperature steam cracking of naphtha to produce lower alkenes and aromatic hydrocarbons. This process significantly increases the yield of high-value products and lowers the yield of low-value products; at the same time, since most of the reactants are converted in catalytic cracking at a relatively low temperature, the overall energy consumption can be lowered.

The process for converting naphtha is characterized in that it at least comprises the following steps:

a) sending a feed that contains naphtha into a first reaction zone to contact and react with a catalyst that contains a molecular sieve at a reaction temperature of 580° C. to 700° C., and separating after the reaction to obtain a material flow I, a material flow II, and a product II;

b) sending a steam and the material flow I obtained in the step a) into a second reaction zone to undergo a steam cracking reaction at a reaction temperature of 780° C. to 870° C., and obtaining a product III after the reaction;

c) returning the material flow II obtained in the step a) to the first reaction zone;

the material flow I comprises alkanes with a carbon atom number of 2 to 5;

the material flow II comprises alkanes with a carbon atom number of 6 to 12 and alkenes with a carbon atom number of 5 to 12;

the product II comprises lower alkenes with a carbon atom number of 2 to 4 and aromatic hydrocarbons with a carbon atom number of 6 to 8;

the product III comprises lower alkenes with a carbon atom number of 2 to 4 and aromatic hydrocarbons with a carbon atom number of 6 to 8.

The reaction products in the first reaction zone are separated to obtain the material flow I, the material flow II, and the product II, and the remainder is a byproduct II. The byproduct II mainly comprises hydrogen gas, methane and aromatic hydrocarbons with a carbon atom number greater than 8.

The lower alkenes with a carbon atom number of 2 to 4 and aromatic hydrocarbons with a carbon atom number of 6 to 8 both have relatively high economic values, and both can be used as important raw materials in chemical industry. The process according to the present application can obtain a lot of the above products with high values from the reaction of the raw material naphtha.

In the reaction products of catalytic cracking in the first reaction zone, the alkanes with a carbon atom number no less than 6 and the alkenes with a carbon atom number no less than 5 can be further converted to lower alkenes and light aromatic hydrocarbon with higher values. When a molecule has many carbon atoms, however, the selectivity is usually low in a steam cracking reaction (relative to catalytic cracking), making it not suitable for steam cracking. As described above, the present application combines catalytic cracking and steam cracking and makes use of advantageous aspects of the two cracking processes, respectively, such that the reactants first undergo a catalytic cracking reaction at relatively low reaction temperature in the first reaction zone, most materials produce reaction products with high values in a highly selective manner, and materials that are suitable for catalytic cracking in the remaining reaction products are transported into the catalytic reactor again for recycling, and materials that are suitable for steam cracking undergo high-temperature steam cracking. The reaction products are output or stored. In one implementation mode of the present application, separation is performed after catalytic cracking in the first reaction zone, wherein alkanes with a carbon atom number of 2 to 5 undergo steam cracking, and moreover, alkanes with a carbon atom number of 6 to 12 and alkenes with a carbon atom number of 5 to 12 are further returned to the first reaction zone for continued catalytic cracking to be converted to lower alkenes and light aromatic hydrocarbon with higher values. Therefore, the present application changes the understanding of applications of recycling and steam cracking in the prior art, and selectively performs steam cracking only on the component of alkanes with a carbon atom number of 2 to 5 with very low economic values, low production and difficulty in catalytic conversion. By only slightly increasing the energy consumption, the present application converts most of the components with very low economic values to products with very high economic values; selectively performs recycled catalytic cracking only on alkanes with a carbon atom number of 6 to 12 and alkenes with a carbon atom number of 5 to 12, and further converts low-value products suitable for catalytic cracking to products with higher values. The technical solution of the present application employs a technical means that applies different processing modes on components with different reaction features, and uses a more suitable and more efficient process to convert a low-value component to a high-value component, which significantly improves the economic advantages as a whole.

Preferably, the range of reaction temperature of the first reaction zone in the step a) has a lower limit selected from 600° C., 640° C. and 670° C., and an upper limit selected from 720° C., 700° C., 680° C. and 670° C. More preferably, the reaction temperature of the first reaction zone in the step a) is from 640° C. to 680° C.

Preferably, the range of weight hourly space velocity of naphtha in the feed to the first reaction zone in the step a) has a lower limit selected from 0.5 h$^{-1}$, 0.8 h$^{-1}$, 1.0 h$^{-1}$, and 1.2 h$^{-1}$, and an upper limit selected from 2.5 h$^{-1}$, 1.6 h$^{-1}$, 1.4 h$^{-1}$, 1.2 h$^{-1}$, and 1.0 h$^{-1}$. More preferably, the weight hourly space velocity of naphtha in the feed to the first reaction zone in the step a) is 0.5 to 2.5 h$^{-1}$.

The feed to the first reaction zone in the step a) can comprise water, and the range of weight ratio of water to naphtha in the feed has a lower limit selected from 0, 0.14, 0.33, 0.6, and 1, and an upper limit selected from 0.6, 1, 1.25, and 1.5. More preferably, the weight ratio of water to naphtha in the feed=0 to 1.5. Further preferably, the weight ratio of water to naphtha in the feed=0 to 1.25. Water can participate in the catalytic cracking process, or catalytic cracking can proceed without water. In the catalytic cracking reaction, steam is not added to the feed, which has the following advantages: in the absence of steam, the molecular sieve will not lose active centers due to the loss of aluminum as the skeleton caused by the high-temperature steam, and the service life of the catalyst will be extended significantly; and moreover, the energy consumption is lowered, and wastewater is reduced. In a preferred implementation manner, the feed to the first reaction zone in the step a) consists of naphtha.

Preferably, the first reaction zone comprises at least one fixed bed reactor. More preferably, the first reaction zone comprises a fixed bed catalytic reaction zone and the heat required for the reaction is supplied by means of external heating.

According to a preferred implementation manner of the present application, a catalyst used in the first reaction zone in the process is provided. The catalyst has excellent single pass reaction performance for naphtha and at the same time, is more suitable for a system of simultaneous reactions of naphtha with alkenes with a carbon atom number no less than 5 and alkanes with a carbon atom number no less than 6. Moreover, it also has great steam stability.

Preferably, in the catalyst that contains a molecular sieve in the step a), the molecular sieve is a hydrogen-type ZSM-5 molecular sieve. The hydrogen-type molecular sieve is obtained through ammonium ion exchange and baking of the molecular sieve.

Preferably, in the catalyst that contains a molecular sieve in the step a), the molecular sieve is a molecular sieve obtained through modification with at least one of lanthanides and/or phosphorus. More preferably, in the modified molecular sieve, the mass percent of lanthanides in the modified molecular sieve is no lower than 6% as oxides; the mass percent of phosphorus in the modified molecular sieve is no lower than 3% as the oxide $P_2O_5$. Further preferably, in the modified molecular sieve, the mass percent of lanthanides in the modified molecular sieve is no lower than 9% as oxides; the mass percent of phosphorus in the modified molecular sieve is no lower than 4% as the oxide $P_2O_5$.

According to a preferred implementation manner, in the catalyst that contains a molecular sieve in the step a), the molecular sieve is a molecular sieve obtained through modification with lanthanum and phosphorus, wherein the mass percent of lanthanum in the modified molecular sieve is 6-12% as the oxide $La_2O_3$; the mass percent of phosphorus in the modified molecular sieve is 3-10% as the oxide $P_2O_5$.

According to a preferred implementation manner, in the catalyst that contains a molecular sieve in the step a), the molecular sieve is a hydrogen-type ZSM-5 molecular sieve obtained through modification with lanthanum and phosphorus, wherein the mass percent of lanthanum in the modified molecular sieve is 6-12% as the oxide $La_2O_3$; the mass percent of phosphorus in the modified molecular sieve is 3-10% as the oxide $P_2O_5$.

Preferably, in the catalyst that contains a molecular sieve in the step a), the molar ratio of silicon to aluminum of the molecular sieve is $SiO_2/Al_2O_3$=20 to 200.

Preferably, in the catalyst that contains a molecular sieve in the step a), the catalyst consists of the modified molecular sieve and aluminum oxide. More preferably, the mass percent of the modified molecular sieve in the catalyst is no lower than 60 wt %. Further preferably, the mass percent of the modified molecular sieve in the catalyst is no lower than 75 wt %.

According to a preferred implementation manner, the weight ratio of water/the material flow II of water and the material flow II entering the second reaction zone in the step c) is 0.3 to 0.5; the temperature range of the second reaction zone is from 800° C. to 850° C.; the retention time of water and the material flow II in the second reaction zone is 0.2 s to 0.5 s. More preferably, the temperature range of the second reaction zone is from 820° C. to 850° C.

The advantageous effects of the present application include:

1) The process according to the present application have both the advantages of catalytic cracking in low reaction temperature and high selectivity and the advantage of steam cracking in converting alkanes with a carbon atom number of 2 to 5.

2) The process according to the present application achieves higher yield of products with high values and lower energy consumption.

DETAILED DESCRIPTION OF THE INVENTION

The present application will be described in detail below with reference to examples, but the present application is not limited to these examples.

Unless specifically described, the raw materials and catalysts in examples of the present application were all purchased commercially, wherein the ZSM-5 molecular sieve was purchased from the Catalyst Factory of Nankai University. The composition of naphtha used in implementation of the present application is shown in Table 1 below:

TABLE 1

| Name of raw material | Normal alkanes (wt %) | Isoalkanes (wt %) | Cycloalkanes (wt %) | Aromatic hydrocarbons (wt %) |
|---|---|---|---|---|
| Naphtha (IBP-150° C.) | 41.04 | 24.23 | 15.26 | 14.49 |
| Naphtha (IBP-180° C.) | 34.97 | 29.31 | 28.12 | 7.60 |

The analytical method in the examples of the present application is as follows:

Reaction products are analyzed by online GC. The GC is Agilent 7890A and detection is performed with Agilent HP-5 capillary columns.

The method for calculating "yield" in the examples of the present application is as follows:

Yield=produced amount of a target product/amount of fed naphtha×100%

The method for calculating "selectivity of (ethylene+propylene+butylene)" in the examples of the present application is as follows:

Selectivity of (ethylene+propylene+butylene)=(ethylene+propylene+butylene)/(hydrogen+hydrocarbons with a carbon atom number of 1 to 4)×100%

In the examples of the present application, the yield and selectivity are all calculated on a weight basis.

Example 1 Preparation of the Catalyst CAT-1#

Preparation of a Modified Molecular Sieve Z-1#

The modified molecular sieve is prepared with the immersion method, specifically: immersing 84 g of a hydrogen-type ZSM-5 molecular sieve having a silicon to aluminum ratio (molar ratio) $SiO_2/Al_2O_3$=50 in 100 ml of an $La(NO_3)_3$ solution with a concentration of 0.74 mol/L, drying in an oven at 120° C., baking at 550° C., then immersing the baked solid in 100 g of a phosphoric acid solution with a concentration of 4 wt %; further drying in an oven at 120° C., baking at 550° C., and obtaining a modified molecular sieve marked as Sample Z-1#. In the Sample Z-1#, the mass percent of $La_2O_3$ is 12%, and the mass percent of $P_2O_5$ is 4%.

Preparation of the Catalyst CAT-1#

Mixing 75 g of the Sample Z-1# and 25 g of aluminum oxide, adding 30 ml 3% diluted nitric acid, stirring and kneading, and extruding to mold; further drying in an oven at 120° C., baking at 650° C., and obtaining a molded catalyst marked as the catalyst CAT-1#. In the catalyst CAT-1#, the mass percent of the Sample Z-1# is 75%, and the mass percent of aluminum oxide is 25%.

Example 2 Preparation of the Catalyst CAT-2#

Preparation of a Modified Molecular Sieve Z-2#

Immersing 84 g of a hydrogen-type ZSM-5 molecular sieve having a silicon to aluminum ratio (molar ratio) $SiO_2/Al_2O_3$=50 in 100 ml of an $La(NO_3)_3$ solution with a concentration of 0.74 mol/L, drying in an oven at 120° C., baking at 550° C., then immersing the baked solid in 100 g of a phosphoric acid solution with a concentration of 4 wt %; further drying in an oven at 120° C., baking at 550° C., and obtaining a modified molecular sieve marked as Sample Z-2#. In the Sample Z-2#, the mass percent of $La_2O_3$ is 12%, and the mass percent of $P_2O_5$ is 4%.

Preparation of the Catalyst CAT-2#

Mixing 80 g of the Sample Z-2# and 20 g of aluminum oxide, adding 40 ml 3% diluted nitric acid, stirring and kneading, and extruding to mold; further drying in an oven at 120° C., baking at 650° C., and obtaining a molded catalyst marked as the catalyst CAT-2#. In the catalyst CAT-2#, the mass percent of the Sample Z-2# is 80%, and the mass percent of aluminum oxide is 20%.

Example 3 Preparation of the Catalyst CAT-3#

Preparation of a Modified Molecular Sieve Z-3#

Immersing 87 g of a hydrogen-type ZSM-5 molecular sieve having a silicon to aluminum ratio (molar ratio) $SiO_2/Al_2O_3$=100 in 100 ml of an $La(NO_3)_3$ solution with a concentration of 0.56 mol/L, drying in an oven at 120° C., baking at 550° C., then immersing the baked solid in 100 g of a phosphoric acid solution with a concentration of 4 wt %; further drying in an oven at 120° C., baking at 550° C., and obtaining a modified molecular sieve marked as Sample Z-3#. In the Sample Z-3#, the mass percent of $La_2O_3$ is 9%, and the mass percent of $P_2O_5$ is 4%.

Preparation of the Catalyst CAT-3#

Mixing 80 g of the Sample Z-3# and 20 g of aluminum oxide, adding 80 ml 3% diluted nitric acid, stirring and kneading, and extruding to mold; further drying in an oven at 120° C., baking at 650° C., and obtaining a molded catalyst marked as the catalyst CAT-3#. In the catalyst CAT-3#, the mass percent of the Sample Z-3# is 80%, and the mass percent of aluminum oxide is 20%.

Examples 4-6 Reaction of Naphtha on the Catalyst CAT-2#

Figure 1:
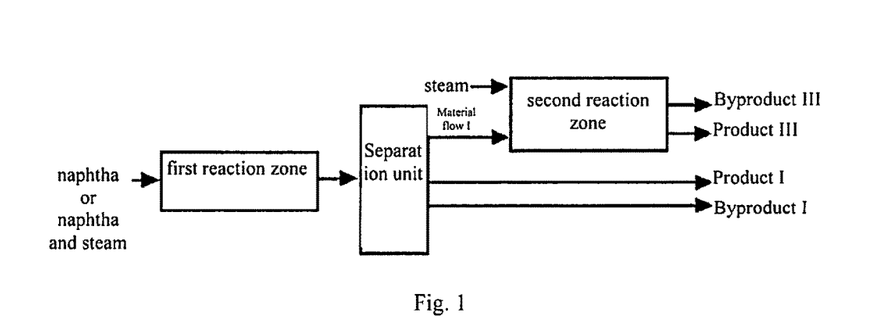
FIG. 1 is a flow chart of an implementation manner of the present application.

The reaction flow is shown in FIG. 1. First, sending the feed of naphtha (IBP—180° C.) and steam into a first reaction zone, the first reaction zone is a fixed bed reactor filled with 10 g of the catalyst CAT-2#, reacting at a reaction temperature of 670° C., and separating the reaction products obtained from the reaction in the first reaction zone to obtain a material flow I, a product I, and a byproduct I, wherein the material flow I comprises alkanes with a carbon atom number of 2 to 5, the product I comprises alkenes with a carbon atom number of 2 to 12, aromatic hydrocarbons with a carbon atom number of 6 to 12, and alkanes with a carbon atom number of 6 to 12, and the remainder is the byproduct I. Sending the material flow I and steam into a steam cracking reactor in a second reaction zone to undergo a steam cracking reaction. The second reaction zone is a tube furnace reactor. Mixing the obtained product III with the chemical products in the product I obtained from the fixed bed reactor of the first reaction zone, wherein the product III obtained from the second reaction zone comprises lower alkenes with a carbon atom number of 2 to 4 and aromatic hydrocarbons with a carbon atom number of 6 to 8, and the remainder is the byproduct III.

See Table 2 for reaction conditions and yields.

TABLE 2

Conditions and yields of reactions of naphtha on the catalyst CAT-2#

| | | Examples | | |
|---|---|---|---|---|
| | | 4 | 5 | 6 |
| Reaction conditions for the first reaction zone | Catalyst | CAT-2# | CAT-2# | CAT-2# |
| | Reaction temperature/° C. | 640 | 670 | 680 |
| | Weight hourly space velocity (WHSV) of naphtha/h$^{-1}$ | 1.0 | 1.2 | 1.4 |
| | | 0.6 | 0.4 | 0.2 |
| | Steam/naphtha (weight ratio) | 0.3 | 0.4 | 0.5 |
| Reaction conditions for the second reaction zone | Steam/material flow I (weight ratio) | 820 | 840 | 850 |
| | Temperature/° C. | 0.2 | 0.4 | 0.5 |
| | Retention time/s | 46.21 | 49.51 | 48.94 |
| First reaction yield, total$^a$ (%) | Gas products, total | 53.33 | 50.02 | 50.57 |
| | Liquid products, total | 0.46 | 0.46 | 0.49 |
| | Coke | | | |
| Gas products and yields in the first reaction zone$^b$ (%) | Hydrogen | 0.37 | 0.37 | 0.39 |
| | Methane | 2.95 | 3.89 | 4.04 |
| | Ethylene | 10.43 | 11.67 | 11.61 |
| | Propylene | 18.37 | 18.06 | 17.22 |
| | Butylene | | | |
| | Ethane | | | |
| | Propane | | | |
| | Butane | | | |
| Liquid products and yields in the first reaction zone (%) | 2-methyl butane | | | |
| | Pentane | | | |
| | Hexane | | | |
| | Heptane | | | |
| | Octane | 6.52 | 6.45 | 6.63 |
| | Nonane | 2.95 | 3.80 | 3.94 |
| | 2-methyl pentane | 2.77 | 3.33 | 3.44 |
| | 3-methyl-pentane | 1.85 | 1.94 | 1.67 |
| | methyl-cyclopentane | 0.47 | 0.49 | 0.75 |
| | 2-methyl-hexane | 0.1 | 0.1 | 0.2 |
| | 2,3-dimethyl-pentane | 5.00 | 3.01 | 3.55 |
| | 3-methyl-hexane | 1.08 | 1.25 | 1.37 |
| | 1,3-dimethyl-cyclopentane | 1.18 | 1.34 | 1.31 |
| | 1,2-dimethyl-cyclopentane | 0.9 | 0.86 | 0.82 |
| | methyl-cyclohexane | 0.73 | 0.76 | 1.13 |
| | 2,4-dimethyl-hexane | 0.40 | 0.46 | 0.61 |
| | 1,2,4-trimethyl-cyclopentane | 0.25 | 0.32 | 0.39 |
| | 1,2,3-trimethyl-cyclopentane | 0.42 | 0.48 | 0.55 |
| | 1,1,2-trimethylcyclopentane | 0.35 | 0.37 | 0.42 |
| | 3-methyl-heptane | 0.69 | 0.77 | 0.89 |
| | cis 1,3-dimethyl-cyclohexane | 0.20 | 0.24 | 0.26 |
| | cis 1,4-dimethylcyclohexane | 0.98 | 1.11 | 1.21 |
| | 1,1-dimethyl-cyclohexane | 1.86 | 2.08 | 2.34 |
| | 1-ethyl I-2 methyl-cyclopentane | 0.23 | 0.25 | 0.26 |
| | | 0.46 | 0.47 | 0.48 |
| | | 0.54 | 0.57 | 0.66 |
| | | 0.24 | 0.38 | 0.39 |
| | | 0.61 | 0.63 | 0.64 |
| | | 1.80 | 1.76 | 1.47 |
| | | | | 0.26 |
| | | 0.23 | 0.23 | 0.22 |
| | | 0.35 | 0.34 | 0.36 |
| | trans 1,2-dimethyl-cyclohexane | 0.85 | 0.80 | 0.78 |
| | cis 1,4-dimethyl-cyclohexane | 0.29 | | 0.29 |
| | trans 1,3-dimethyl-cyclohexane | | 0.28 | |
| | 2,4-dimethyl-heptane | 0.26 | 0.25 | |
| | cis 1,2-dimethyl-cyclohexane | 0.20 | | |
| | ethyl-cyclohexane | 1.23 | 1.14 | 1.11 |
| | 1,1,3-trimethylcyclohexane | 1.39 | 1.21 | 1.15 |
| | 3,5-dimethyl-heptane | | | 0.30 |
| | 2,5-dimethyl-heptane | 0.41 | 0.31 | |
| | 1-ethyl-2-methyl-cyclohexane | 0.24 | 0.21 | |
| | 1,2,4-trimethyl-cyclohexane | 0.51 | 0.44 | 0.38 |
| | 2,3-dimethyl-heptane | 0.71 | 0.61 | 0.53 |
| | 3-methyl-octane | 0.30 | | |
| | 1,1,2-trimethyl-cyclohexane | 0.12 | | |
| | 1-ethyl-3-methylcyclohexane | 0.57 | 0.47 | 0.42 |
| | 1-ethyl-4-methyl-cyclohexane | 0.19 | | |
| | cis bicyclononane | 0.27 | 0.20 | 0.00 |
| | 2,6-dimethyl-octane | 0.28 | | |
| | benzene | 1.26 | 2.02 | 2.51 |
| | toluene | 3.97 | 5.63 | 5.96 |
| | p-xylene | 3.04 | 3.21 | 3.07 |
| | o-xylene | 1.02 | 1.10 | 1.00 |

TABLE 2-continued

Conditions and yields of reactions of naphtha on the catalyst CAT-2#

|  |  | Examples | | |
|---|---|---|---|---|
|  |  | 4 | 5 | 6 |
|  | ethylbenzene | 0.21 | 0.24 | 0.00 |
|  | 1-ethyl-3-methyl-benzene | 0.20 |  | 0.23 |
|  | 1,2,3-trimethyl-benzene | 0.34 |  |  |
|  | naphthalene | 0.25 | 0.00 | 0.00 |
|  | Others (content <0.5%) | 3.60 | 2.48 | 1.09 |
| Statistics on yields of main products in the first reaction zone (%) | ethylene + propylene + butylene (%) | 35.32 | 36.26 | 35.47 |
|  | Selectivity of (ethylene + propylene + butylene) (%) propylene/ethylene | 76.43 | 73.24 | 72.49 |
|  | BTX$^c$ (%) | 1.76 | 1.55 | 1.48 |
|  | ethylene + propylene + butylene + BTX (%) | 8.86 | 11.39 | 12.3 |
|  | ethane + propane + butane + pentane (%) | 44.18 | 47.65 | 47.77 |
|  | N-alkanes with a carbon atom number ≥C6 | 21.22 | 21.22 | 21.26 |
|  | Isoalkanes and cycloalkanes | 8.16 | 6.46 | 7.05 |
|  | Other aromatic hydrocarbons and trace components | 17.89 | 16.94 | 17.5 |
| Products and yields in the second reaction zone (%) | ethylene | 4.77 | 3.08 | 1.51 |
|  | propylene | 8.46 | 8.64 | 8.67 |
|  | butylene | 3.4 | 3.23 | 3.22 |
|  | butadiene | 0.39 | 0.38 | 0.38 |
|  | BTX | 0.75 | 0.72 | 0.73 |
|  |  | 0.37 | 0.41 | 0.43 |
| Total yields of the first and second reaction zones (%) | lower alkenes + BTX (%) | 57.55 | 61.03 | 61.2 |
|  | gasoline with high octane number | 30.81 | 26.48 | 26.06 |
|  | Total | 88.38 | 87.51 | 87.26 |

Note
$^a$all yields in the table are percent yields by weight.

Note
$^b$BTX refers to light aromatic hydrocarbon, comprising benzene, toluene and xylene.

Note
$^c$C$_{6-12}$ alkanes refer to alkanes with a carbon atom number of 6 to 12.

From the data in Table 2, it can be seen that, at a reaction temperature of 670° C., naphtha goes through one catalytic cracking reaction, and alkanes with a carbon atom number from 2 to 5 in the products undergo steam cracking and recycling. The total yield of the final chemical products (lower alkenes+BTX) and gasoline with high octane number (other liquid products after BTX is removed) reaches up to 87 to 88%.

Example 7 Reaction on the Catalyst CAT-2# in the First Reaction Zone without Steam The reaction flow is the same as that in Example 4, except that no steam is added in the first reaction zone. The reaction flow is shown in FIG. 1. The reaction results of naphtha (IBP-180° C.) at 670° C. are listed in Table 3.

TABLE 3

Conditions and yields of reactions of naphtha on the catalyst CAT-2# with no addition of water

| Example 7 | Catalyst | CAT-2$^#$ |
|---|---|---|
| Reaction conditions for the first reaction zone | Temperature/° C. | 670 |
|  | Weight hourly space velocity (WHSV) of naphtha/h$^{-1}$ | 1.6 |
|  | Steam/naphtha (w/w) | 0 |
| Reaction conditions for the second reaction zone | ratio of the material flow I to steam | 0.4 |
|  | Temperature/° C. | 820 |
|  | Retention time/s | 0.3 |
| Total reaction yield$^a$ (%) | Gas products, total (%) | 57.99 |
|  | Liquid products, total (%) | 41.46 |
|  | Coke (%) | 0.55 |
| Gas products and yields in the first reaction zone (%)$^b$ | Hydrogen (%) | 0.83 |
|  | Methane (%) | 5.87 |
|  | Ethylene (%) | 12.84 |
|  | Propylene (%) | 20.18 |
|  | Butylene (%) | 7.26 |
|  | Ethane (%) | 4.59 |
|  | Propane (%) | 4.04 |
|  | Butane | 2.39 |
|  | Total yield of gas products | 57.99 |
| Liquid products in the first reaction zone (%) | 2-methyl butane | 0.65 |
|  | Pentane | 9.2 |
|  | Hexane | 2.07 |
|  | Heptane | 0.78 |
|  | Octane | 0.46 |
|  | 2-methyl pentane | 0.68 |
|  | 3-methyl pentane | 0.42 |
|  | methyl-cyclopentane | 0.21 |
|  | 2,3-dimethyl-pentane | .32 |
|  | 3 methyl-hexane | .53 |
|  | trans 1,2-dimethyl-cyclopentane methyl-cyclohexane |  |
|  | 1,2,4-trimethyl-cyclopentane | 0.93 |
|  | 1,2,3-trimethyl-cyclopentane | 1.36 |
|  | 3-methyl-heptane | 0.30 |
|  | cis 1,3-dimethyl-cyclohexane | 0.40 |
|  | 1-ethyl-2-methyl-cyclopentane | 0.32 |
|  | trans 1,2-dimethyl-cyclohexane | 0.76 |
|  | ethyl-cyclohexane | 0.18 |
|  | 1,1,3-trimethylcyclohexane | 0.43 |
|  | 2,3-dimethyl heptane | 0.48 |
|  | benzene | 0.53 |
|  | toluene | 0.27 |

TABLE 3-continued

Conditions and yields of reactions of naphtha on the catalyst CAT-2# with no addition of water

| Example 7 | Catalyst | CAT-2# |
|---|---|---|
| | p-xylene | 4.68 |
| | o-xylene | 7.65 |
| | ethylbenzene | 3.49 |
| | 1,2,3-trimethyl benzene | 1.13 |
| | naphthalene | 0.29 |
| | Others (content <0.5%) | 0.32 |
| Statistics on main products in the first reaction zone (%) | ethylene + propylene + butylene (%) | 0.17 |
| | Selectivity of (ethylene + propylene + butylene) (%) | 2.57 |
| | propylene/ethylene | 40.28 |
| | BTX$^c$ (%) | 69.46 |
| | ethylene + propylene + butylene + BTX (%) | 1.57 |
| | | 16.97 |
| | C2-C5 alkanes that can be cracked by steam | 57.26 |
| | ≥C6, normal alkanes | 20.77 |
| | Isoalkanes and cycloalkanes | 3.31 |
| | Other aromatic hydrocarbons and trace components | 8.12 |
| | | 3.31 |
| Products and yields in the second reaction zone (%) | ethylene | 5.36 |
| | propylene | 1.34 |
| | butylene | 0.32 |
| | butadiene | 0.66 |
| | BTX | 0.42 |
| Total yields of the first and second reaction zones (%) | lower alkenes + BTX (%) | 65.36 |
| | gasoline with high octane number | 14.74 |
| | Total | 80.1 |

Note
$^a$all yields in the table are percent yields by weight.

Note
$^b$BTX refers to light aromatic hydrocarbon, comprising benzene, toluene and xylene.

Note
$^c$C$_{6-12}$ alkanes refer to alkanes with a carbon atom number of 6 to 12.

It can be seen that, when no steam is added in the catalytic cracking reaction in the first reaction zone, the selectivity is lowered to a degree and the methane yield increases to a degree, but the yield of "lower alkenes+BTX" in the catalytic cracking products increases. This is because the catalyst activity is higher and the conversion rate of reactants is increased when there is no steam. The decreasing selectivity of the catalytic cracking reaction leads to the decreased total yield of the target products, which is still up to 80%.

Figure 3:
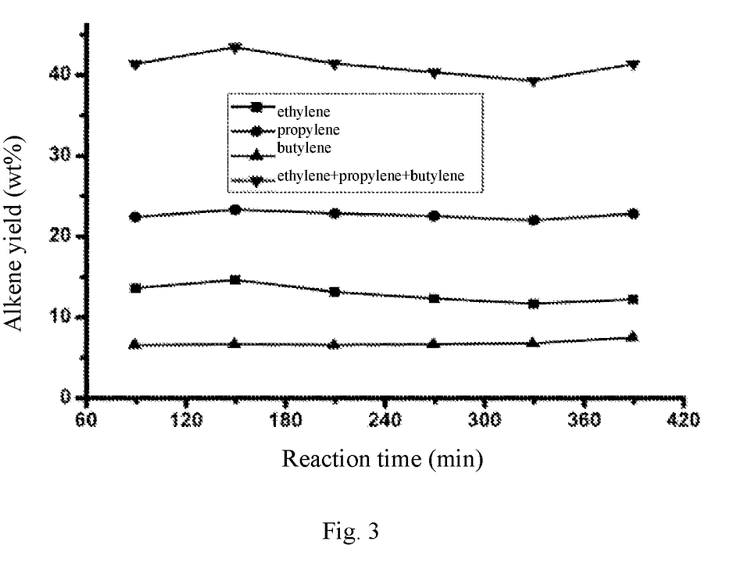
FIG. 3 is a diagram of changes to lower alkenes in the reaction products vs. reaction time when there is no steam in the feed onto a catalyst CAT-2# in Example 7.

See FIG. 3 for changes to lower alkenes in the catalytic reaction products vs. reaction time.

Figure 2:
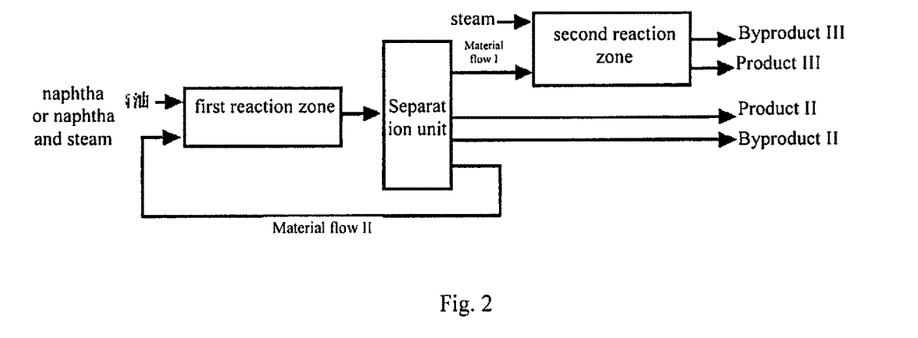
FIG. 2 is a flow chart of an implementation manner of the present application.

Examples 8-10 Reactions of Naphtha on Different Catalysts Using Catalytic Cracking and Recycling The reaction flow is shown in FIG. 2. First, sending the feed of naphtha (IBP—150° C.) and steam into a first reaction zone. In Example 8, Example 9 and Example 10, the first reaction zones are filled, respectively, with 10 g of the catalyst CAT-1#, the catalyst CAT-2#, and the catalyst CAT-3# prepared in Examples 1, 2, and 3, all of which are fixed bed reactors. The reaction products obtained from the reaction in the first reaction zone are separated to obtain a material flow I, a material flow II, a product II, and a byproduct II, wherein the material flow I comprises alkanes with a carbon atom number of 2 to 5, the material flow II comprises alkanes with a carbon atom number of 6 to 12 and alkenes with a carbon atom number of 5 to 12, the product II comprises lower alkenes with a carbon atom number of 2 to 4 and aromatic hydrocarbons with a carbon atom number of 6 to 8, and the remainder is the byproduct II. Returning the material flow II to the fixed bed reactors in the first reaction zone to continue the catalytic cracking reaction. Sending the material flow I and steam into a steam cracking reactor in a second reaction zone to undergo a steam cracking reaction. The second reaction zone is a tube furnace reactor, and both the obtained product III and the product II obtained from the fixed bed reactor of the first reaction zone are used as chemical products, wherein the product III obtained from the second reaction zone comprises lower alkenes with a carbon atom number of 2 to 4 and aromatic hydrocarbons with a carbon atom number of 6 to 8, and the remainder is the byproduct III.

See Table 4 for reaction temperature, weight ratio of water to naphtha (IBP—150° C.), and weight hourly space velocity of naphtha in the feed, and other conditions are the same as those in Example 4. The results of reactions of naphtha (IBP—150° C.) on different catalysts are listed in Table 4.

Table 4 Conditions and yields of reactions on different catalysts in Examples 8-10

TABLE 4

Conditions and yields of reactions on different catalysts in Examples 8-10

| | | Examples | | |
|---|---|---|---|---|
| | | 8 | 9 | 10 |
| Reaction conditions for the first reaction zone | Catalyst | CAT-1# | CAT-2# | CAT-3# |
| | Temperature/° C. | 640 | 670 | 680 |
| | Weight hourly space velocity (WHSV) of naphtha/h$^{-1}$ | 0.8 | 0.8 | 0.8 |
| | WHSV of steam/h$^{-1}$ | 0.8 | 1.0 | 1.5 |
| Reaction conditions for the second reaction zone | Steam/material flow I (weight ratio) | 1 | 0.35 | 0.4 |
| | Temperature/° C. | 800 | 820 | 840 |
| | Retention time/s | 0.25 | 0.3 | 0.35 |
| Reaction yields in the first reaction zone$^a$ | Gas products, total (%) | 58.77 | 68.1 | 55.36 |
| | Liquid products, total (%) | 40.95 | 31.52 | 44.35 |
| | Coke (%) | 0.28 | 0.38 | 0.42 |
| Gas products and yields in the first reaction zone (%)$^b$ | Hydrogen (%) | 0.37 | 0.38 | 0.29 |
| | Methane (%) | 3.4 | 3.83 | 3.25 |
| | Ethylene (%) | 13.62 | 16.46 | 11.95 |
| | Propylene (%) | 30.3 | 33.2 | 29.3 |
| | Butylene (%) | 8.0 | 8.9 | 7.7 |
| | Ethane (%) | 4.42 | 4.69 | 3.82 |
| | Propane (%) | 4.14 | 4.59 | 3.44 |
| | Butane | 2.58 | 2.39 | 2.39 |

TABLE 4-continued

Conditions and yields of reactions on different catalysts in Examples 8-10

|  |  | Examples | | |
|---|---|---|---|---|
|  |  | 8 | 9 | 10 |
| Liquid products and yields in the first reaction zone (%) | 2-methyl butane | 0.23 | 0.12 | 0.43 |
|  | Pentane | 8.39 | 8.56 | 8.59 |
|  | Hexane | 1.39 | 1.46 | 1.93 |
|  | Heptane | 1.00 | 044 | 1.57 |
|  | Nonane | 0.62 | 0.25 | 0.97 |
|  | dimethyl pentane | 0.52 | 0.36 | 0.84 |
|  | trimethyl pentane | 0.34 | 0.23 | 0.53 |
|  | dimethyl hexane | 0.42 | 0.25 | 0.61 |
|  | 2,3-dimethyl-pentane | 0.34 | 0.27 | 0.35 |
|  | trimethyl hexane | 0.60 | 0.36 | 0.77 |
|  | triethyl pentane |  | 0.12 |  |
|  | 1,2-dimethyl cyclopentane | 0.31 | 0.24 | 0.31 |
|  | methyl-cyclohexane | 0.61 | 0.39 | 0.61 |
|  | 2-methyl-3-ethyl pentane | 0.47 | 0.24 | 0.34 |
|  | 1,2,4-trimethyl cyclopentane | 0.20 | 0.15 | 0.19 |
|  | 1,2,3-trimethyl cyclopentane |  | 0.17 | 0.21 |
|  | 3-ethyl-2-methyl pentane | 0.36 | 0.37 | 0.48 |
|  | 3-methyl heptane | 0.72 | 0.42 | 0.82 |
|  | cis 1,3-dimethyl cyclohexane | 0.44 | 0.38 | 0.52 |
|  | 1-ethyl-2-methyl cyclopentane | 0.28 | 0.20 | 0.28 |
|  | 1,2-dimethyl cyclohexane | 0.24 | 0.18 | 0.23 |
|  | 2,4-dimethyl heptane | 0.93 | 0.34 | 1.49 |
|  | 2,3,4-trimethyl hexane | 0.28 | 0.16 | 0.22 |
|  | ethyl cyclohexane | 0.84 | 0.55 | 0.84 |
|  | 1,2,3-trimethyl cyclohexane | 0.43 | 0.28 | 0.37 |
|  | 2,5-dimethyl heptane | 0.56 | 0.39 | 0.55 |
|  | 2,3-dimethyl heptane | 0.84 | 0.49 | 0.76 |
|  | 3-ethyl heptane | 0.18 | 0.13 |  |
|  | 3-methyl octane | 0.38 | 0.19 | 0.49 |
|  | 1-ethyl-3-methylcyclohexane | 0.40 | 0.25 | 0.36 |
|  | 2,6-dimethyl octane | 0.47 | 0.32 | 0.47 |
|  | 2-methyl-3-ethyl heptane | 0.42 | 0.29 | 0.40 |
|  | benzene | 1.54 | 1.45 | 1.67 |
|  | toluene | 4.59 | 3.38 | 4.46 |
|  | p-xylene | 3.96 | 2.77 | 3.98 |
|  | o-xylene | 1.58 | 1.18 | 1.54 |
|  | 1-ethyl-2-methyl benzene | 0.69 | 0.39 | 0.49 |
|  | 1,2,3-trimethyl benzene | 0.27 | 0.17 | 0.28 |
|  | 1-ethyl-4-methyl benzene | 0.45 | 0.25 | 0.33 |
|  | 1,2,4-trimethyl benzene | 0.49 | 0.34 | 0.45 |
|  | 3-methyl styrene | 0.22 | 0.17 | 0.70 |
|  | piperidine | 0.41 | 0.19 | 0.37 |
|  | Others (content <0.5%) | 3.93 | 2.65 | 4.36 |
| Statistics on main products | ethylene + propylene + butylene (%) | 43.76 | 52.12 | 42.17 |
|  | Selectivity of (ethylene + propylene + butylene) (%) | 74.46 | 76.53 | 76.17 |
|  | propylene/ethylene | 1.65 | 1.64 | 1.86 |
|  | BTX[b] (%) | 11.68 | 8.80 | 11.66 |
|  | ethylene + propylene + butylene + BTX (%) | 55.45 | 60.92 | 53.83 |
|  | C2-C5 alkanes that can be cracked by steam | 19.75 | 20.35 | 18.66 |
|  | ≥C6, normal alkanes | 3.01 | 2.15 | 5.04 |
|  | Isoalkanes and cycloalkanes | 11.58 | 7.72 | 13.04 |
|  | Other aromatic hydrocarbons and trace components | 6.07 | 4.17 | 5.6 |
| Products and yields in the second reaction zone (%) | ethylene | 8.20 | 8.47 | 7.70 |
|  | propylene | 2.83 | 2.90 | 2.74 |
|  | butylene | 0.30 | 0.30 | 0.30 |
|  | butadiene | 0.62 | 0.63 | 0.60 |
|  | BTX | 0.40 | 0.41 | 0.40 |
| Total | Chemical products from steam cracking | 12.35 | 12.71 | 11.74 |
| Products of secondary catalytic cracking of $C_{6-12}$ alkanes[c] (%) | ethylene | 2.04 | 1.38 | 2.52 |
|  | propylene | 4.38 | 2.96 | 5.41 |
|  | butylene | 1.17 | 0.79 | 1.44 |
|  | BTX | 1.60 | 1.09 | 1.98 |

TABLE 4-continued

Conditions and yields of reactions on different catalysts in Examples 8-10

|  |  | Examples | | |
|---|---|---|---|---|
|  |  | 8 | 9 | 10 |
| Total | Chemical products from secondary catalytic cracking | 9.19 | 6.21 | 11.35 |
| Total yields of the | ethylene | 23.86 | 26.31 | 22.17 |
| first and second | propylene | 37.51 | 39.06 | 37.45 |
| reaction zones (%) | butylene | 9.47 | 9.99 | 9.44 |
|  | butadiene | 0.62 | 0.63 | 0.60 |
|  | BTX | 13.68 | 10.3 | 14.04 |
|  | Total | 85.14 | 86.29 | 83.7 |

Note
[a] all yields in the table are percent yields by weight.
Note
[b] BTX refers to light aromatic hydrocarbon, comprising benzene, toluene and xylene.
Note
[c] $C_{6-12}$ alkanes refer to alkanes with a carbon atom number of 6 to 12.

After the catalytic cracking reaction on naphtha in the first reaction zone, the steam cracking and recycling of the material flow I and the catalytic recycling of the material flow 2, the total yield of chemical products on different catalysts can reach 83 to 85%.

Figure 4:
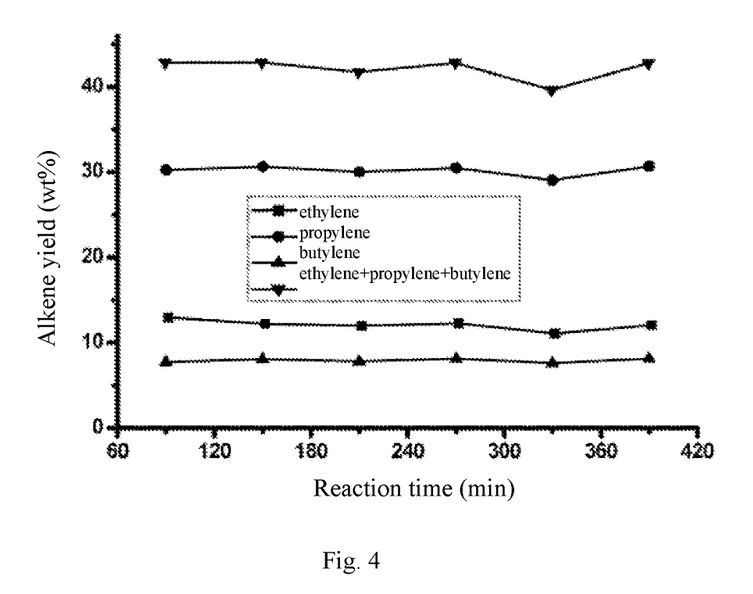
FIG. 4 is a diagram of changes to lower alkenes in the reaction products vs. reaction time on a catalyst CAT-1# in Example 8.
Figure 5:
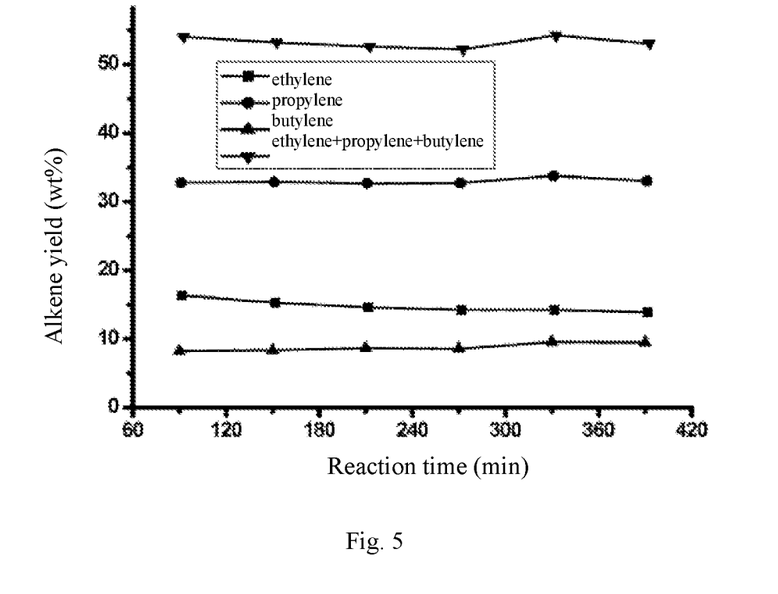
FIG. 5 is a diagram of changes to lower alkenes in the reaction products vs. reaction time on the catalyst CAT-2# in Example 9.
Figure 6:
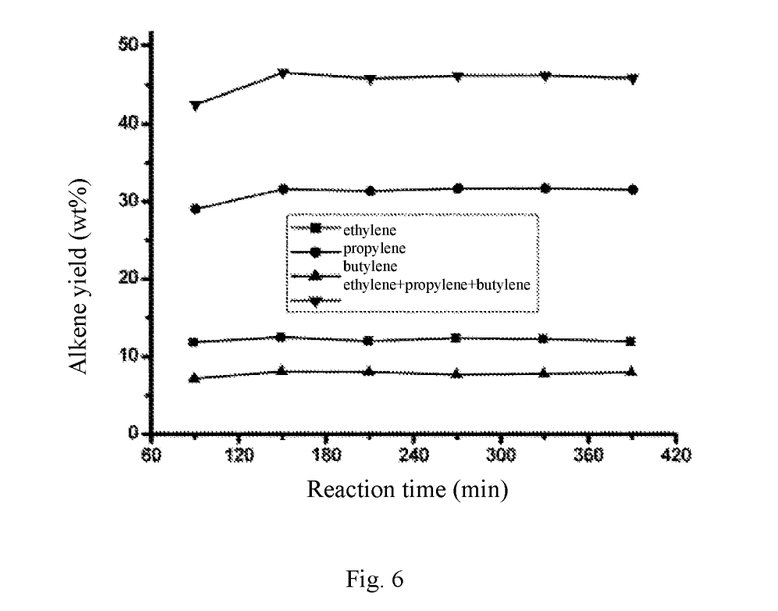
FIG. 6 is a diagram of changes to lower alkenes in the reaction products vs. reaction time on a catalyst CAT-3# in Example 10.

FIG. 4, FIG. 5 and FIG. 6 are diagrams of changes to lower alkenes in the first catalytic reaction products vs. reaction time in Example 8, Example 9 and Example 10, respectively.

Only a few embodiments of the present application are described above, which are not intended to limit the present application in any form. Although the present application is disclosed with the preferred embodiments as above, they are not used to limit the present application. Variations or modifications made by a person skilled in the art by using the above disclosed technical content and without departing from the technical solutions of the present application are equivalent implementation cases and shall be encompassed by the technical solutions.

The invention claimed is:

1. A process for converting naphtha, the process comprising the steps of:
   a) sending a feed that contains naphtha into a first reaction zone to contact and react with a catalyst that contains a molecular sieve at a reaction temperature of 580° C. to 700° C. to produce reaction products, and separating the reaction products to obtain a material flow I and a product I;
   b) sending steam and the material flow I obtained in step a) into a second reaction zone to undergo a steam cracking reaction at a reaction temperature of 780° C. to 870° C., and obtaining a product III after the reaction;
   wherein the material flow I comprises alkanes with a carbon atom number of 2 to 5, wherein the alkanes with a carbon atom number of 2 to 5 comprise ethane, propane, butanes and pentanes;
   wherein the product I comprises alkenes with a carbon atom number of 2 to 12, aromatic hydrocarbons with a carbon atom number of 6 to 12, and alkanes with a carbon atom number of 6 to 12; and
   wherein the product III comprises lower alkenes with a carbon atom number of 2 to 4 and aromatic hydrocarbons with a carbon atom number of 6 to 8.

2. The process according to claim 1, wherein the reaction temperature of the first reaction zone in step a) is from 640° C. to 680° C.

3. The process according to claim 1, wherein the feed in step a) further comprises steam, and the weight ratio of steam to naphtha in the feed is from greater than 0 to 1.5.

4. The process according to claim 1, wherein, in the catalyst that contains a molecular sieve in step a), the molecular sieve is H-ZSM-5 molecular sieve.

5. The process according to claim 1, wherein, in the catalyst that contains a molecular sieve in step a), the molecular sieve is a molecular sieve obtained through modification with a lanthanide, phosphorus, or both.

6. The process according to claim 1, wherein, in step a) the catalyst that contains a molecular sieve, the molecular sieve comprises silica and alumina, and the molar ratio of the silica to the alumina of the molecular sieve is 20 to 200.

7. The process according to claim 1, wherein the weight ratio of steam and the material flow I entering the second reaction zone in step b) is 0.2 to 0.5; the temperature range of the second reaction zone is from 800° C. to 850° C.; and the retention time of steam and the material flow I in the second reaction zone is 0.2 s to 0.5 s.

8. A process for converting naphtha, the process comprising the steps of:
   a) sending a feed that contains naphtha into a first reaction zone to contact and react with a catalyst that contains a molecular sieve at a reaction temperature of 580° C. to 700° C. to produce reaction products, and separating the reaction products to obtain a material flow I, a material flow II, and a product II;
   b) sending steam and the material flow I obtained in step a) into a second reaction zone to undergo a steam cracking reaction at a reaction temperature of 780° C. to 870° C., and obtaining a product III after the reaction;
   c) returning the material flow II obtained in step a) to the first reaction zone;
   wherein the material flow I comprises alkanes with a carbon atom number of 2 to 5, wherein the alkanes with a carbon atom number of 2 to 5 comprise ethane, propane, butanes and pentanes;
   wherein the material flow II comprises alkanes with a carbon atom number of 6 to 12 and alkenes with a carbon atom number of 5 to 12;

wherein the product II comprises lower alkenes with a carbon atom number of 2 to 4 and aromatic hydrocarbons with a carbon atom number of 6 to 8; and wherein the product III comprises lower alkenes with a carbon atom number of 2 to 4 and aromatic hydrocarbons with a carbon atom number of 6 to 8.

9. The process according to claim 2, wherein the weight hourly space velocity of naphtha in the feed to the first reaction zone in step a) is 0.5 $h^{-1}$ to 2.5 $h^{-1}$.

10. The process according to claim 8, wherein the feed in step a) further comprises steam, and the weight ratio of steam to naphtha in the feed is from greater than 0 to 1.5.

11. The process according to claim 8, wherein, in the catalyst that contains a molecular sieve in step a), the molecular sieve is a H-ZSM-5 molecular sieve.

12. The process according to claim 8, wherein, in the catalyst that contains a molecular sieve in step a), the molecular sieve is a molecular sieve obtained through modification with a lanthanide, phosphorus, or both.

13. The process according to claim 8, wherein, in the catalyst that contains a molecular sieve in step a), the molecular sieve is a molecular sieve modified with lanthanum and phosphorus, and wherein the mass percent of lanthanum in the modified molecular sieve is 6-12% as the oxide $La_2O_3$ and the mass percent of phosphorus in the modified molecular sieve is 3-10% as the oxide $P_2O_5$.

14. The process according to claim 8, wherein in step a) the catalyst that contains a molecular sieve comprises alumina and silica, and wherein the molar ratio of silica to alumina of the molecular sieve is 20 to 200.

15. A process for converting naphtha, the process comprising the steps of:
 a) sending a feed that contains naphtha into a first reaction zone to contact and react with a catalyst that contains a molecular sieve at a reaction temperature of 580° C. to 700° C. to produce reaction products, and separating the reaction products to obtain a material flow I and a product I;
 b) sending steam and the material flow I obtained in step a) into a second reaction zone to undergo a steam cracking reaction at a reaction temperature of 780° C. to 870° C., and obtaining a product III after the reaction;
 wherein the material flow I comprises alkanes with a carbon atom number of 2 to 5;
 wherein the product I comprises alkenes with a carbon atom number of 2 to 12, aromatic hydrocarbons with a carbon atom number of 6 to 12, and alkanes with a carbon atom number of 6 to 12; and
 wherein the product III comprises lower alkenes with a carbon atom number of 2 to 4 and aromatic hydrocarbons with a carbon atom number of 6 to 8, wherein, in the catalyst that contains a molecular sieve in step a), the molecular sieve is a molecular sieve modified with lanthanum and phosphorus, and wherein the mass percent of lanthanum in the modified molecular sieve is 6-12% as the oxide $La_2O_3$ and the mass percent of phosphorus in the modified molecular sieve is 3-10% as the oxide $P_2O_5$.

* * * * *